United States Patent
Li

(10) Patent No.: US 11,446,518 B2
(45) Date of Patent: Sep. 20, 2022

(54) MULTI-LEAF COLLIMATOR AND RADIATION THERAPY HEAD

(71) Applicant: OUR UNITED CORPORATION, Shaanxi (CN)

(72) Inventor: Jinsheng Li, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 118 days.

(21) Appl. No.: 16/649,347

(22) PCT Filed: Sep. 20, 2017

(86) PCT No.: PCT/CN2017/102523
§ 371 (c)(1),
(2) Date: Mar. 20, 2020

(87) PCT Pub. No.: WO2019/056230
PCT Pub. Date: Mar. 28, 2019

(65) Prior Publication Data
US 2020/0230437 A1    Jul. 23, 2020

(51) Int. Cl.
*A61N 5/10*    (2006.01)

(52) U.S. Cl.
CPC ......... *A61N 5/1047* (2013.01); *A61N 5/1067* (2013.01)

(58) Field of Classification Search
CPC ...... A61N 5/1042–1047; A61N 5/1036–1039; A61N 5/1064; A61N 5/1067; A61N 5/1065; A61N 5/1068–107; A61N 2005/1095; G21K 1/046; G21K 5/00; G21K 5/04; H05H 7/001; H05H 2007/007; H05H 2277/11
See application file for complete search history.

(56) References Cited

U.S. PATENT DOCUMENTS

| | | |
|---|---|---|
| 5,591,983 A | 1/1997 | Yao |
| 8,637,841 B2 | 1/2014 | Prince et al. |
| (Continued) | | |

FOREIGN PATENT DOCUMENTS

| | | |
|---|---|---|
| CN | 1139580 A | 1/1997 |
| CN | 101927061 A | 12/2010 |
| (Continued) | | |

OTHER PUBLICATIONS

International search report of PCT application No. PCT/CN2017/102523 dated May 30, 2018.

*Primary Examiner* — John P Lacyk
(74) *Attorney, Agent, or Firm* — Knobbe Martens Olson & Bear LLP

(57) ABSTRACT

A multi-leaf collimator includes a driving component, a controller and n leaf-group layers, where n is an integer greater than or equal to 2, wherein each leaf-group layer includes one group of leaves or two opposing groups of leaves, each group of leaves includes a plurality of leaves, each of the leaves includes a front end surface and a rear end surface which are opposite to each other, and each of the leaves is movable so that the front end surfaces of the leaves in the multiple leaf-group layers form a variable-shaped region that allows beams to pass through; and the rear end surface of the leaf is connected to the driving component, and the controller is configured to control the driving component to drive the leaf to move.

20 Claims, 5 Drawing Sheets

(56) References Cited

U.S. PATENT DOCUMENTS

| | | | |
|---|---|---|---|
| 2001/0043669 A1* | 11/2001 | Ein-Gal | A61N 5/1042 378/152 |
| 2002/0101959 A1* | 8/2002 | Kato | A61N 5/1042 378/152 |
| 2012/0043482 A1* | 2/2012 | Prince | A61N 5/1045 250/505.1 |
| 2017/0084359 A1* | 3/2017 | Constantin | G21K 1/046 |
| 2017/0087387 A1* | 3/2017 | Nord | G21K 1/046 |
| 2017/0148536 A1* | 5/2017 | Kawrykow | A61N 5/1077 |
| 2019/0022409 A1* | 1/2019 | Vanderstraten | A61N 5/1081 |

FOREIGN PATENT DOCUMENTS

| | | | |
|---|---|---|---|
| CN | 102915784 A | | 2/2013 |
| CN | 103079643 A | | 5/2013 |
| CN | 103272338 A | | 9/2013 |
| CN | 105703526 A | | 6/2016 |
| CN | 106730421 A | * | 5/2017 |

\* cited by examiner

MULTI-LEAF COLLIMATOR AND RADIATION THERAPY HEAD

CROSS-REFERENCE TO RELATED APPLICATION

This application is a National Phase of International Application No. PCT/CN2017/102523 filed on Sep. 20, 2017 and entitled "MULTI-LEAF COLLIMATOR AND RADIATION TREATMENT HEAD, the entire contents of which are incorporated herein by reference.

TECHNICAL FIELD

The present disclosure relates to the field of medical devices, and more particularly to a multi-leaf collimator and a radiation therapy head.

BACKGROUND

In modern medicine, radiation therapy is an important means to treat malignant tumors. The radiation therapy uses high-energy radioactive rays to kill tumors. Currently, a radiation therapy head is mainly used for radiation therapy. The radiation therapy head generally includes a ray source and a radiation field collimation system, and a multi-leaf collimator is part of the radiation field collimation system. Exemplarily, the ray source may be an accelerator for emitting X-rays. The multi-leaf collimator is configured to generate a radiation field that meets requirements. The radiation field defines a ray radiation range with certain area and shape which is irradiated by the X-rays. The X-rays emitted by the accelerator are irradiated to a tumor lesion site through the radiation field generated by the multi-leaf collimator.

SUMMARY

The present disclosure provides a multi-leaf collimator and a radiation therapy head.

According to a first aspect of the embodiments of the present disclosure, a multi-leaf collimator is provided. The multi-leaf collimator includes a driving component, a controller, and n leaf-group layers, where n is an integer greater than or equal to 2, wherein each leaf-group layer includes one group of leaves or two opposing groups of leaves, each group of leaves includes a plurality of leaves, each of the leaves includes a front end surface and a rear end surface which are opposite to each other, and each of the leaves is movable so that the front end surfaces of the leaves in the multiple leaf-group layers form a variable-shaped region that allows beams to pass through; and the rear end surface of the leaf is connected to the driving component, and the controller is configured to control the driving component to drive the leaf to move.

According to a second aspect of the embodiments of the present disclosure, a radiation therapy head is provided. The radiation therapy head includes a ray source and a radiation field collimation system.

The ray source is configured to emit beams, and the radiation field collimation system includes any multi-leaf collimator according to the first aspect.

According to a third aspect of the embodiments of the present disclosure, a method for driving a multi-leaf collimator is provided. The method is applied to the multi-leaf collimator according to the first aspect. The method includes:

determining, according to a treatment plan, a target radiation field to be formed;

inquiring, from a preset corresponding relationship between radiation fields and driving modes, a target driving mode corresponding to the target radiation field; and controlling, according to the target driving mode, the leaves to move.

According to a fourth aspect of the embodiments of the present disclosure, an apparatus for driving a multi-leaf collimator is provided. The apparatus includes:

a processor; and a memory for storing an instruction executable by the processor, wherein the processor is configured to:

determine, according to a treatment plan, a target radiation field to be formed;

inquire, from a preset corresponding relationship between radiation fields and driving modes, a target driving mode corresponding to the target radiation field; and control, according to the target driving mode, leaves to move.

According to a fifth aspect of the embodiments of the present disclosure, a storage medium having an instruction stored therein is provided. When running on a terminal, the storage medium causes the terminal to execute the method for driving the multi-leaf collimator according to the above third aspect.

According to a sixth aspect of the embodiments of the present disclosure, a terminal program product containing an instruction is provided. When running on a terminal, the terminal program product causes the terminal to execute the method for driving the multi-leaf collimator according to the above third aspect.

BRIEF DESCRIPTION OF THE DRAWINGS

In order to describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skill in the art may also derive other drawings from these accompanying drawings without creative efforts.

FIG. 3-1 is a schematic structural diagram of a multi-leaf collimator according to an embodiment of the present disclosure;

FIG. 3-2 is a front view of the leaf groups in two layers shown in FIG. 3-1;

FIG. 3-3 is a schematic diagram of leaf groups in two layers according to an embodiment of the present disclosure;

FIG. 6-1 is a schematic structural diagram of an integrated guide rail according to an embodiment of the present disclosure; and FIG. 6-2 is a flowchart of a method for driving a multi-leaf collimator according to an embodiment of the present disclosure.

DETAILED DESCRIPTION

In order to describe the objects, technical solutions and advantages of the present disclosure more clearly, the present disclosure will be further described in detail below in combination with the accompanying drawings. Apparently, the described embodiments are merely some embodiments, rather than all embodiments, of the present disclosure. Based on the embodiments of the present disclosure, all other embodiments derived by a person of ordinary skill in the art without creative efforts shall fall within the protection scope of the present disclosure.

Figure 1:
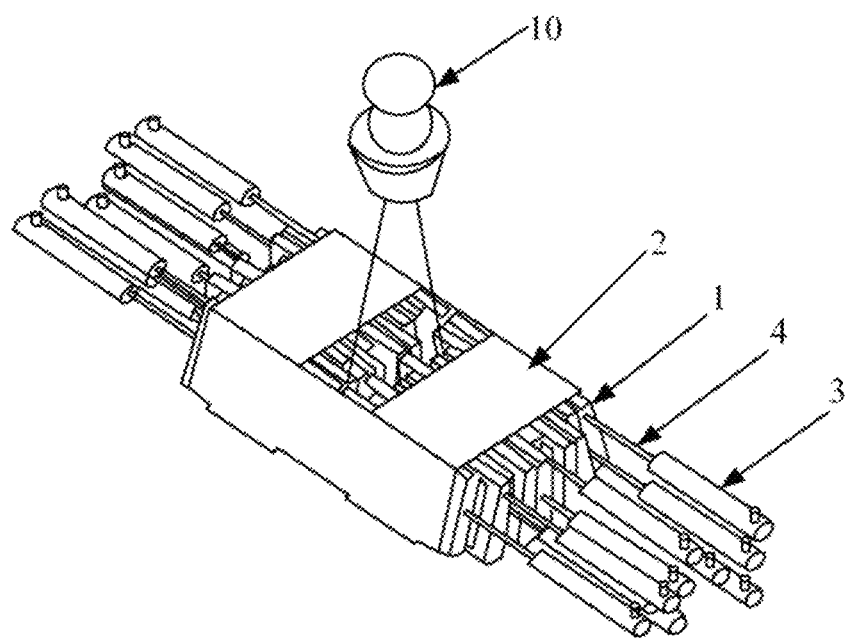
FIG. 1 is a schematic structural diagram of a multi-leaf collimator in the related art.

In the related art, the multi-leaf collimator, as shown in FIG. 1, includes two groups of leaves 1, a transmission rod 4, a motor 3, a controller (not shown in FIG. 1) and a guide rail frame 2. Here, the two groups of leaves are disposed in a same layer, and each group includes a plurality of leaves arranged in an array. A gap is formed between the two groups of leaves for the passage of rays emitted by the ray source 10. Two groups of guide rails in a one-to-one correspondence with the two groups of leaves are disposed in the guide rail frame 2. Each group of guide rails includes a plurality of guide rails disposed in parallel. One leaf is vertically placed on each guide rail for the sliding of the leaf on the guide rail, and the end, away from the gap, of each leaf is connected with the motor 3 through the transmission rod 4. The controller controls, according to a treatment plan, the motor 3 to drive the transmission rod 4, thereby driving, through the transmission rod 4, the corresponding leaf to move along the guide rail to form the radiation field.

In the process of implementing the present disclosure, the inventor found that at least the following problems were present in the prior art.

As the multi-leaf collimator only includes one layer of leaves, the leaves have a relatively larger height and thus a relatively larger mass. As a result, the leaves cannot be easily driven by the driving components and the movement speed of the leaves is relatively low. Thus, on the one hand, the requirements on the strength of the driving components for driving the leaves are relatively higher and hence it is not easy to manufacture the driving components; and on the other hand, the formed radiation field only has limited shapes due to the smaller number of the leaves.

The present disclosure provides a multi-leaf collimator and a radiation therapy head, and may at least solve the problems in the related art that, as the multi-leaf collimator only includes one layer of leaves, the requirements on the strength of the driving components for driving the leaves are relatively higher and thus the driving components cannot be easily manufactured; and the formed radiation field only has limited shapes due to the smaller number of leaves.

Figure 2:
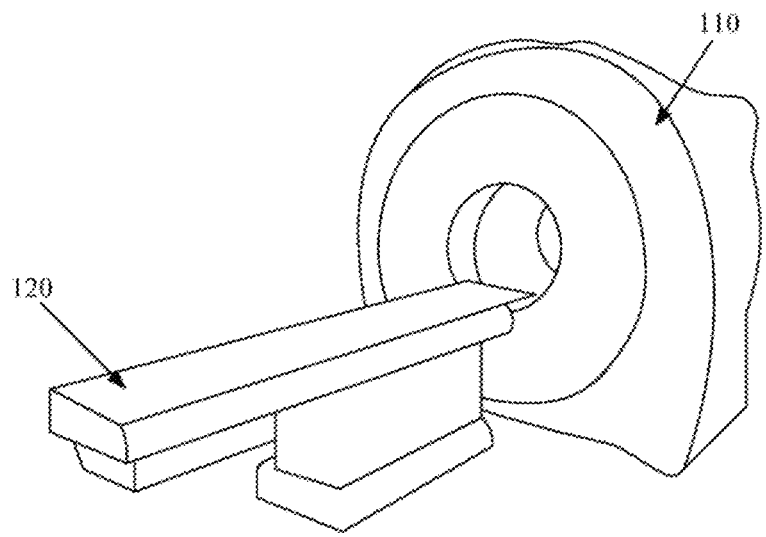
FIG. 2 is a schematic diagram of an implementation environment involved in an embodiment of the present disclosure.

With reference to FIG. 2 which shows a schematic diagram of an implementation environment involved in an embodiment of the present disclosure. The implementation environment may include a rack 110 and a treatment table 120. A radiation therapy head (not drawn in FIG. 2) is disposed on the rack 110 and may rotate along with the rack 110. The rack 110 may be a drum-type rack and may also be a C-arm, a cantilever-type, a semi-arc rack or the like. The radiation therapy head generally includes a ray source and a radiation field collimation system. The ray source may be an X-ray source (which may be an accelerator ray source generally) or an isotope ray source (which may be a cobalt source generally). Taking an accelerator configured to emit X-ray as an example, the radiation field collimation system may include a multi-leaf collimator configured to generate a radiation field that meets requirements. The X-rays emitted by the accelerator are irradiated to a tumor lesion site of a patient by passing through the radiation field generated by the multi-leaf collimator.

Figures 1, 3:
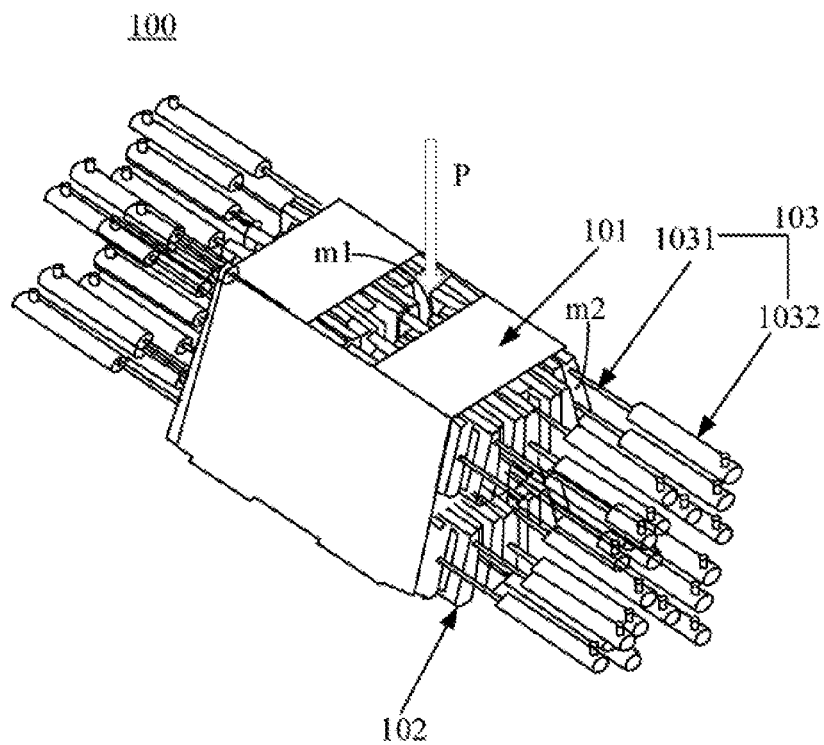
Figures 2, 3:
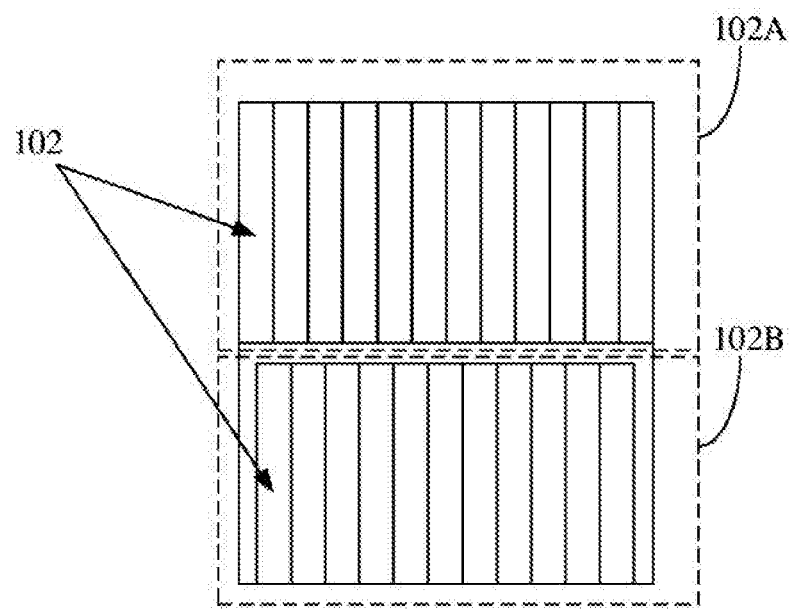
Figure 3:
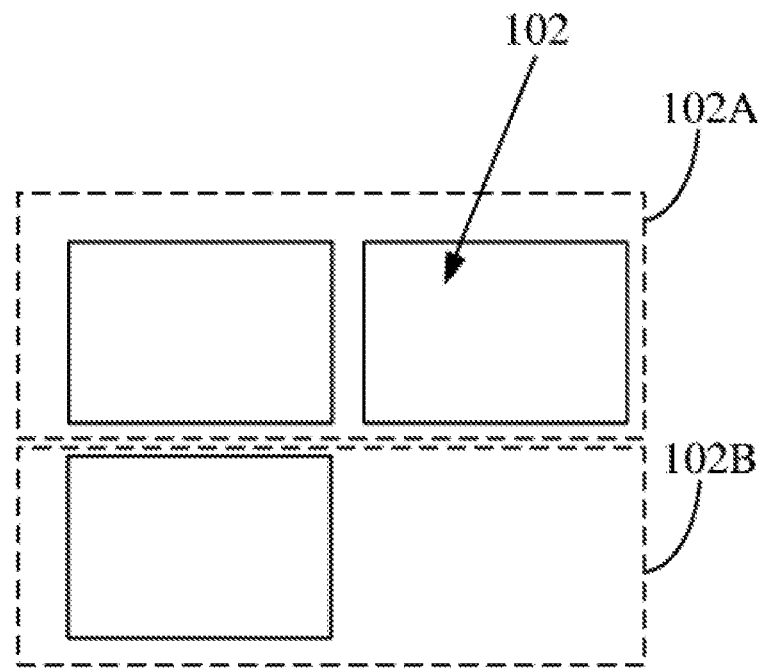

With reference to FIG. 3-1 which shows a schematic structural diagram of a multi-leaf collimator 100 according to an embodiment of the present disclosure. The multi-leaf collimator 100 includes n leaf-group layers (leaf groups in two layers are taken as an example in FIG. 3-1), driving components 103 and a controller (not shown in FIG. 3-1), where n is an integer greater than or equal to 2.

Each leaf-group layer includes one group of leaves or two opposing groups of leaves. Each group of leaves includes a plurality of leaves 102. Each of the leaves 102 includes a front end surface m1 and a rear end surface m2 which are opposite to each other. Each of the leaves 102 can move so that the front end surfaces m1 of the leaves in the multiple layers of leaf groups may form a variable-shaped region that allows beams P to pass through.

The rear end surfaces m2 of the leaves 102 are connected to the driving components 103, and the controller is configured to control the driving components 103 to drive the leaves 102 to move.

FIG. 3-1 is illustrated by taking leaf groups in two layers as an example. FIG. 3-2 shows a front view of the two-layer leaf groups shown in FIG. 3-1. With reference to FIG. 3-2, the two leaf-group layers are leaf groups 102A and 102B, respectively. Each leaf-group layer includes two opposing groups of leaves and each group of leaves includes a plurality of leaves 102.

Exemplarily, a multi-leaf collimator including two leaf-group layers is taken as an example, as shown in FIG. 3-3, the first leaf-group layer 102A may include two opposing groups of leaves, and the second leaf-group layer 102B may include one group of leaves, and the front end surfaces of the leaves in the two leaf-group layers 102A and 102B form a variable-shaped region that allows beams P to pass through. Or, the first leaf-group layer includes two groups of leaves, the second leaf-group layer also includes two groups of leaves, and the front end surfaces of the two groups of leaves included in each leaf-group layer form a variable-shaped region that allows beams to pass through. Or, the first leaf-group layer includes one group of leaves, the second leaf-group layer also includes one group of leaves, these two groups of leaves are staggered in position, and the front end surfaces of these two groups of leaves form a variable-shaped region that allows beams to pass through. Of course, the multi-leaf collimator may also include three or four leaf-group layers, and each leaf-group layer may include one or two groups of leaves, which is not exemplified here.

With the movement of the leaves, the shape of the region that can be passed through by the beams formed by the front end surfaces of the leaves changes correspondingly, so that a conformal radiation field adapted to a treatment plan is formed.

As the multi-leaf collimator according to the embodiment of the present disclosure includes the leaf groups in multiple layers, the leaves in each leaf-group layer have a relatively smaller height and a relatively smaller mass. Hence, the leaves can be easily driven by the driving components, and the driving component can drive the leaf more quickly and the movement speed of the leaves can be relatively higher. Ultimately, on the one hand, the requirements on the strength of the driving components for driving the leaves are relatively lower and thus it is convenient to manufacture the driving components. On the other hand, the driving components can have a relatively smaller size, thus, the leaves can be made thinner. Thus, there can be more leaves. Moreover, the more the leaves are, the more precise the radiation field formed by the leaves is and the more shapes the formed radiation field can have. When the present disclosure is compared with the related art, exemplarily, it is unnecessary to divide a concave radiation field into a plurality of radiation sub-fields and thus the radiation field can be formed more flexibly. In addition, the larger number of leaves also facilitates adjustment on the ray intensity. Moreover, when the movement conditions of leaves in different layers are different, for example, the movement positions may be different, the purposes of adjusting the intensity of the rays that are passed through and adjusting the ray dose can also be achieved. Therefore, when the leaves of the multi-leaf collimator are driven to move, based on the dose distribution at different positions, the positions of the leaves can be adjusted correspondingly.

In practical application, the number of leaf-group layers may be adjusted according to the treatment plan, and thus the number of leaf-group layers (i.e., the value of n) is not limited in the embodiment of the present disclosure.

In summary, in the multi-leaf collimator according to the embodiment of the present disclosure, n leaf-group layers are included in the multi-leaf collimator, where n is an integer greater than or equal to 2, and each leaf-group layer includes one group of leaves or two opposing groups of leaves. Exemplarily, the multi-leaf collimator includes two leaf-group layers, wherein the first leaf-group layer includes one group of leaves, the second leaf-group layer includes two groups of leaves, and each group of leaves includes a plurality of leaves. As the leaves are arranged in multiple layers, the leaves in each layer have a relatively smaller height and mass. Hence, it is easier to drive the leaves, the movement speed of the leaves can be relatively higher, and thus the difficulty in manufacturing the driving component can be reduced. Moreover, as the driving component has a relatively smaller size and thickness, more leaves can be disposed, thus, the leaves can form a more precise radiation field with more shapes. Therefore, the radiation field can be formed more flexibly. In addition, due to the multiple layers of leaves, the adjustments on the ray intensity and ray dose can also be achieved.

Figure 4:
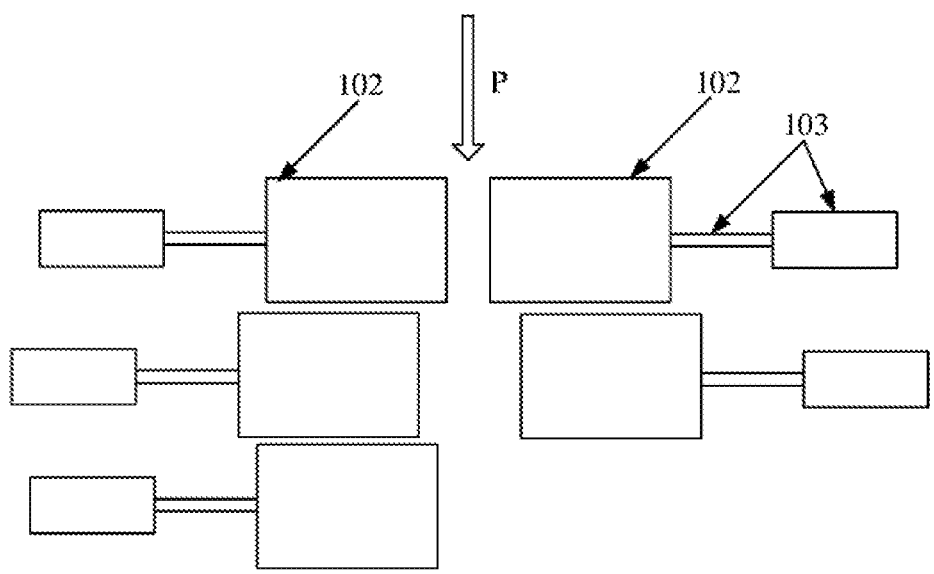
FIG. 4 is a schematic structural diagram of leaf groups in three layers according to an embodiment of the present disclosure.

Optionally, at least one of the n leaf-group layers includes two opposing groups of leaves. Thus, the two groups of leaves in a same layer may form a region with a conformal shape that can be passed through by the beams, and each of other layers may have one group or two groups of leaves for use in the adjustment of dose. FIG. 4 is a side view of a multi-leaf collimator according to an embodiment of the present disclosure and exemplarily shows a schematic structural diagram of leaf groups in three layers. As shown in FIG. 4, the first leaf-group layer includes two groups of leaves, the second leaf-group layer includes two groups of leaves, and the third leaf-group layer includes one group of leaves, and each group of leaves includes a plurality of leaves 102. The plurality of leaves in each group are parallel to one another, and front end surfaces of the leaves form a variable-shaped region that allows beams P to pass through. Here, the first leaf-group layer may form the region that allows beams to pass through, and the second leaf-group layer and the third leaf-group layer may adjust the dose through the movement of leaves. It should be noted that in FIG. 4, only one leaf is shown in each group and the remaining leaves in the respective group are parallel to the leaf as shown.

In practical application, in order to form a radiation field having more shapes, in the n leaf-group layers, the leaves in the same layer have the same height and the leaves in different layers may have the same height or different heights. FIG. 4 is illustrated by taking an example that, the leaves in the same layer of the n leaf-group layers have the same height and the leaves in different layers also have the same height. Exemplarily, when the leaves in the same layer have the same height and the leaves in different layers also have the same height, each leaf may have a height between 5 and 40 mm.

When the leaves in different leaf-group layers have the same height, the adjustment on the ray intensity can be achieved by adjusting the positions of the leaves. When the leaves in different leaf-group layers have different heights, the leaves in different layers have distinguishing degrees of attenuation on the rays, and thus the adjustment on the ray intensity may further be achieved.

Optionally, in the n leaf-group layers, any two adjacent leaf-group layers may be detachably connected. In practical applications, according to tumor situations of different patients, the leaf groups may be removed or replaced before treatment according to treatment demands, so that the treatment on the different patients may be better optimized.

It should also be noted that in the related art, the ray intensity is generally adjusted by controlling the ray source. To be specific, the ray intensity may be adjusted by controlling the number of rays emitted by the ray source or controlling the duration during which the ray source emits the rays. The multi-leaf collimator cannot achieve the adjustment on the ray intensity.

However, in the embodiments of the present disclosure, since the multi-leaf collimator includes the multiple layers of leaves which are combined and stacked, the multi-leaf collimator can achieve the purpose of adjusting the ray intensity by adjusting the combined thickness of the multiple layers of leaves. For example, when the leaves in different leaf-group layers have the same height but different movement positions, the leaves at different position can attenuate the intensity of the rays emitted by the ray source to different degrees, thereby achieving the effect of modulating the ray intensity distribution. In another example, when the leaves in different leaf-group layers have different heights, the leaves at different positions may have more variations in the combined thickness, so that more choices can be provided when adjusting the ray intensity. As compared with the mode that the ray intensity in the radiation field is modulated by overlapping a plurality of radiation sub-fields of different shapes, in the mode that the intensity-modulated treatment is achieved by attenuating the ray intensity to modulate the ray intensity in the radiation field, the treatment time is shorter, the treatment efficiency is higher and the total quantity of radiations emitted by the ray source is lower.

Exemplarily, the leaves in each leaf-group layer may have a thickness of less than 5 mm. In addition, the leaves in the same leaf-group layer may have the same thickness or different thicknesses, and the leaves in different leaf-group layers may have the same thickness or different thicknesses, which is not limited in the embodiment of the present disclosure.

Exemplarily, the leaves in each leaf-group layer may have a height between one-tenth and four times of a half-value layer of a ray, whereas in the related art, the height of the leaves of the multi-leaf collimator is generally greater than six times of the half-value layer of the ray.

Further, as shown FIG. 3-1, the multi-leaf collimator further includes guide rails (not drawn in FIG. 3-1) and a guide rail frame 101. The leaves 102 are disposed on the guide rails and can move along the guide rails. Each leaf-group layer is disposed in one guide rail frame, and in the n leaf-group layers, the guide rail frames of any two adjacent layers may be detachably connected. In this way, it is convenient to remove and replace the leaves of the multi-leaf collimator so as to meet different treatment demands. The guide rails may be disposed in the guide rail frame, or, the guide rails and the guide rail frame may be fixedly connected to each other.

Or, the n leaf-group layers may be disposed in one guide rail frame, and the guide rails of each leaf-group layer are detachably connected with the guide rail frame. Any two adjacent guide rail frames are detachably connected. In this way, the guide rail frame can be removed according to the treatment plan to decrease the number of layers, or a guide rail frame may be added according to the treatment plan to increase the number of the layers. The number of the guide rail frames is not limited in the embodiment of the present disclosure.

Figure 5:
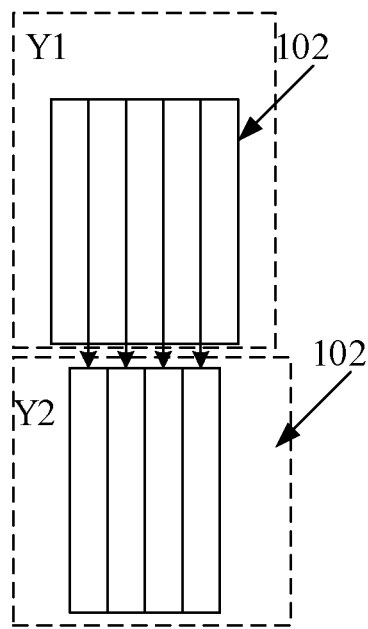
FIG. 5 is a schematic structural diagram of leaf groups in two layers according to an embodiment of the present disclosure.

Optionally, in order to prevent the rays emitted by the ray source from leaking via a gap between the leaves in the upper layer to affect the treatment effect, in an embodiment of the present disclosure, for weakening the phenomenon of ray leakage between the leaves, in the n leaf-group layers, the leaves in any two layers have the same movement direction and orthographic projections of leaves in different layers in a beam direction partially overlap or do not overlap. That is, the gaps between the leaves in a group are not in alignment with the gaps between the leaves in a group of a different layer, and the leaves in different leaf-group layers are staggered. Exemplarily, FIG. 5 is a sectional view of a multi-leaf collimator according to an embodiment of the present disclosure and shows a schematic structural diagram of leaves in two layers. FIG. 5 is illustrated by taking an example that the leaves in the same layer have the same thickness and the leaves in different layers also have the same thickness. With reference to FIG. 5, an orthographic projection of the leaves in the upper leaf-group layer Y1 in the beam direction partially overlaps with an orthographic projection of the leaves in the lower leaf-group layer Y2 in the beam direction, that is, the leaves are staggered in position, so that the rays transmitted from the gaps between the leaves on the upper layer can be shielded by the leaves on the lower layer and thus the rays are prevented from leaking from the gaps between the leaves.

In addition, in the field of radiation therapy technologies, the spatial resolution of the formed radiation field of the multi-leaf collimator depends on the thickness of the leaves. The thinner the leaves are, the higher the spatial resolution of the formed radiation field (i.e., the spatial resolution at the edge of the radiation field) is. However, the leaf thickness always has a limit value. Hence, in order to increase the spatial resolution of the formed radiation field, in the embodiment of the present disclosure, in the n leaf-group layers, the orthographic projections of the leaves in different layers in the beam direction partially overlap or do not overlap. Exemplarily, with reference to FIG. 5, an orthographic projection of the leaves in the upper leaf-group layer Y1 in the beam direction partially overlaps with an orthographic projection of the leaves in the lower leaf-group layer Y2 in the beam direction. The staggering and overlapping manner of different layers of leaves can be used to improve the spatial resolution at the edge of the radiation field, so that the radiation field has a more precise size. In this way, during tumor treatment, it is more beneficial to avoid sensitive healthy tissues around the tumors.

Optionally, the leaves in a same leaf-group layer have the same movement direction, and the leaves in different leaf-group layers have different movement directions. In the multi-leaf collimator, the leaves in the same leaf-group layer may move in the same direction and the leaves in different leaf-group layers may move in the same direction or in different directions. In order to further form the radiation field having more shapes, the leaves in the same leaf-group layer may move in the same direction and the leaves in different leaf-group layers may move in different directions. By arranging the leaves in different leaf-group layers to move in different directions, the radiation field can be formed into any shape and a plurality of radiation sub-fields can also be formed. In one possible implementation mode, in the multi-leaf collimator, the guide rails in the same layer have the same direction and the guide rails in different layers have different directions. For example, the guide rails in different layers may have an inclined angle of 90 degrees, 30 degrees, 60 degrees or the like. In addition, such an arrangement mode of the guide rails also facilitates the adjustment on ray intensity and the improvement on the spatial resolution of the formed radiation field. In another possible implementation mode, a corresponding connection angle of leaf groups may be a preset angle including a particular inclined angle.

Figures 1, 6:
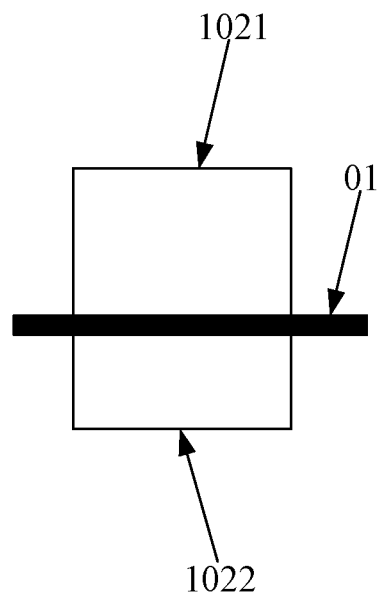
Figures 2, 6:
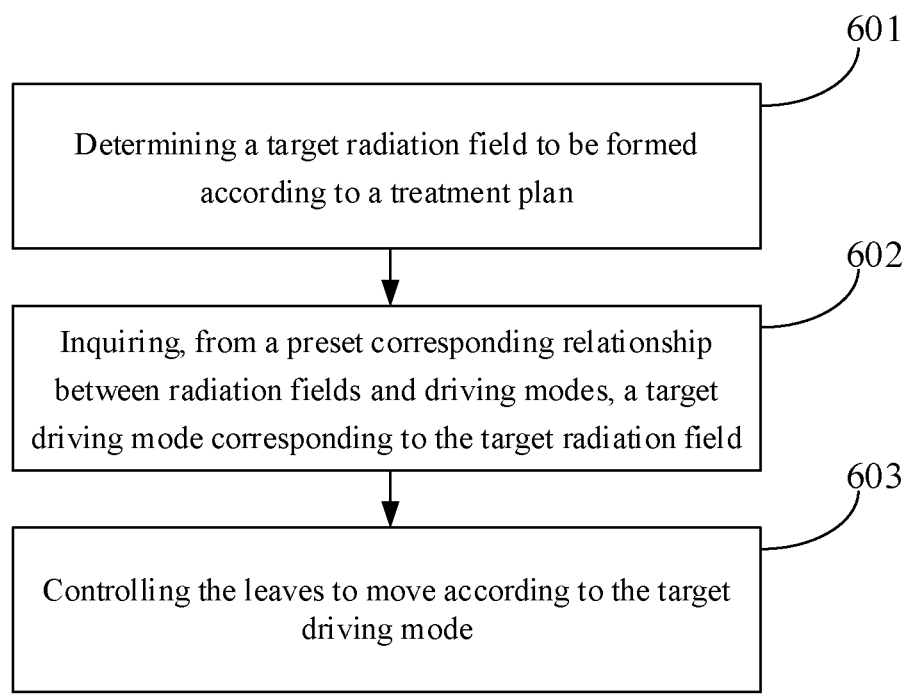

Further, in order to reduce the structural complexity of the multi-leaf collimator, the guide rails corresponding to two leaves, on a same plane, located in two adjacent leaf-group layers can be integrated. In this way, the layers of the guide rail can be reduced. Exemplarily, as shown in FIG. 6-1, it is assumed that the multi-leaf collimator includes two leaf-group layers, as such, tracks may be arranged on both upper and lower sides of a guide rail respectively. That is, the guide rails 01 corresponding to both the leaf 1021 and the leaf 1022 are integrated. FIG. 6-1 is illustrated by taking an example that the leaves in different leaf-group layers have different heights.

Optionally, as shown in FIG. 3-1, a driving component 103 includes a transmission rod 1031 and a motor 1032. The rear end surface of each leaf 102 is connected to a motor 1032 through a transmission rod 1031, and the controller is configured to control the motor 1032 to drive the transmission rod 1031, so as to drive the leaf 102 to move. The respective leaves in the multi-leaf collimator can move independently under the control of the controller and the driving components.

In the embodiment of the present disclosure, the controller of the multi-leaf collimator may pre-store a corresponding relationship between radiation fields and driving modes. One radiation field corresponds to at least one driving mode. The driving mode is configured to indicate the movement parameter of each leaf in the n leaf-group layers, when the corresponding radiation field is to be formed. The movement parameter may include a movement speed and a movement displacement. Exemplarily, the plurality of driving modes may include a driving mode of adjusting the dose via movement speed of the leaves, and may also be a driving mode of adjusting the dose via displacement of the leaves.

When the multi-leaf collimator according to the embodiment of the present disclosure is used for radiation therapy, a driving method of the multi-leaf collimator may include: determining, by the controller, according to a treatment plan, a radiation field to be formed; then looking for, from the pre-stored corresponding relationship between the radiation fields and the driving modes, by the controller, a driving mode corresponding to the radiation field to be formed as determined; and next, controlling, by the controller, according to the inquired driving mode, the driving components to drive the leaves to move along the guide rails. When multiple driving modes are found, the controller may select any one from the multiple driving modes.

As the multi-leaf collimator according to the embodiment of the present disclosure includes leaf groups in multiple layers, the leaves have a relatively smaller height and a relatively smaller mass. Hence, the leaves can be easily driven by the driving components, the movement speed of the leaves can be relatively higher, and thus the requirements on the strength of the driving components for driving the leaves are relatively lower. As the driving components have a relatively smaller size and the leaves are thinner, more leaves can be disposed. In addition, the leaves in different leaf-group layers may have different heights, may be staggered and may have different movement directions. By means of such multi-leaf collimator, all of the one-dimensional wedge-shaped ray intensity distribution and dose distribution as well as the two-dimensional wedge-shaped ray intensity distribution and dose distribution can be formed. Therefore, the treatment plan can be greatly optimized, and a better treatment plan for treatment can be produced, which thus brings more possibilities for improving the quality of treatment plan and treatment effect.

In summary, in the multi-leaf collimator according to the embodiment of the present disclosure, the multi-leaf collimator includes n leaf-group layers, where n is an integer greater than or equal to 2; and each leaf-group layer includes one or two groups of leaves (for example, the multi-leaf collimator may include two leaf-group layers, wherein the first leaf-group layer includes one group of leaves, and the second leaf-group layer includes two groups of leaves), and each group of leaves includes a plurality of leaves. As the leaves are arranged in multiple layers, the leaves in each layer have a relatively smaller height and mass. Hence, it is easier to drive the leaves and the movement speed of the leaves can be relatively higher and thus the difficulty in manufacturing the driving components can be reduced. Moreover, as the driving components have a relatively smaller size and thickness, more leaves can be disposed, thus, the leaves can form a more precise radiation field with more shapes. Therefore, the radiation field can be formed more flexibly. In addition, due to the multiple layers of leaves, the adjustments on the ray intensity and ray dose can also be achieved.

An embodiment of the present disclosure further provides a radiation therapy head including a ray source and a radiation field collimation system.

The ray source is configured to emit beams.

The radiation field collimation system includes the multi-leaf collimator shown in FIG. 3-1.

The ray source may be an X-ray source or a y-ray source. The multi-leaf collimator is configured to generate a radiation field that meets requirements. The rays emitted by the ray source are irradiated to a tumor lesion site of a patient through the radiation field generated by the multi-leaf collimator.

An embodiment of the present disclosure further provides a method for driving a multi-leaf collimator. The method is applied to the multi-leaf collimator shown in FIG. 3-1. The method can be executed by the controller of the multi-leaf collimator. As shown in FIG. 6-2, the method includes the following steps.

In step 601, a target radiation field to be formed is determined according to a treatment plan.

In step 602, a target driving mode corresponding to the target radiation field is inquired from a preset corresponding relationship between radiation fields and driving modes. Exemplarily, one radiation field may correspond to a plurality of driving modes and any of these driving modes can be selected as the target driving mode. Exemplarily, the plurality of driving modes may include the driving mode of adjusting the dose via the movement speed of the leaves, or the driving mode of adjusting the dose via the displacement of the leaves.

In step 603, leaves are controlled to move according to the target driving mode.

In summary, in the method for driving the multi-leaf collimator according to the embodiment of the present disclosure, the target radiation field to be formed is determined according to the treatment plan; the target driving mode corresponding to the target radiation field is inquired from the preset corresponding relationship between the radiation fields and the driving modes; and the leaves are controlled to move according to the target driving mode. As compared with the related art, the method can form a radiation field having more shapes and improve the flexibility in forming the radiation field.

Steps 601-603 may be executed by the controller of the multi-leaf collimator.

Step 603 may include controlling, according to the target driving mode, the driving components to drive the leaves to move along the guide rails.

Optionally, the target driving mode may be configured to indicate that the leaves from different leaf-group layers move at different speeds. Correspondingly, step 603 may include: controlling, according to the target driving mode, the leaves from different leaf-group layers to move at different movement speeds.

Exemplarily, the multi-leaf collimator includes one guide rail frame and two leaf-group layers. The two leaf-group layers are located in the guide rail frame, and each leaf-group layer includes two groups of leaves. When the leaves are controlled to move according to the target driving mode, the leaves in the first layer may be controlled to move at speed v1 and the leaves in the second layer may be controlled to move at speed v2, wherein v2 and v1 may be the same or different.

Optionally, the target driving mode may be configured to indicate that the leaves in the same leaf-group layer perform reciprocating movement in the same direction and the leaves in different leaf-group layers perform reciprocating movement in different directions. Correspondingly, step 603 may include: according to the target driving mode, the leaves in the same leaf-group layer are controlled to perform reciprocating movement in the same direction and the leaves in different leaf-group layers are controlled to perform reciprocating movement in different directions. In the embodiment of the present disclosure, the leaves in the same leaf-group layer may move in the same direction and the leaves in different leaf-group layers may move in different directions or in the same direction.

In the embodiment of the present disclosure, the various leaf-group layers may be controlled by the controller directly or by the controller through sub-controllers. Each leaf-group layer corresponds to one sub-controller. Correspondingly, step 603 may include controlling, according to the target driving mode, the leaves in a leaf-group layer to move, through the corresponding sub-controller. All the sub-controllers are controlled by one controller. Exemplarily, the multi-leaf collimator includes one guide rail frame and two leaf-group layers and each leaf-group layer includes two groups of leaves. The multi-leaf collimator includes the two leaf-group layers, wherein the leaves in the first layer correspond to a sub-controller C10, and the leaves from the second layer correspond to a sub-controller C20. When the controller controlling the leaves to move according to the target driving mode, the leaves in the first leaf-group layer can be controlled by the sub-controller C10 to move and the leaves in the second leaf-group layer can be controlled by the sub-controller C20 to move.

In addition, each leaf may correspond to one sub-controller and the various leaves in various leaf-group layers may move independently under control of the controller and the sub-controllers.

It should be noted that the sequence of the steps in the method for driving the multi-leaf collimator according to the embodiment of the present disclosure may be adjusted appropriately, and the steps may be correspondingly deleted or added according to the situation. Any derived method easily conceived by a person skilled in the art within the technical scope disclosed in the present disclosure shall fall within the protection scope of the present disclosure, which is not repeated here.

In summary, in the method for driving the multi-leaf collimator according to the embodiment of the present disclosure, the target radiation field to be formed can be determined according to the treatment plan; the target driving mode corresponding to the target radiation field is inquired from the preset corresponding relationship between the radiation fields and the driving modes; and the leaves are controlled to move according to the target driving mode. When this driving method is compared with the related art, the radiation field having more shapes can be formed and the radiation field can be formed more flexibly. In addition, the effect of adjusting the ray intensity can be achieved, the treatment efficiency is higher and the spatial resolution of the formed radiation field is higher. Therefore, the treatment plan can be greatly optimized, and a better treatment plan for treatment can be produced, which thus brings more possibilities for improving the quality of treatment plan and treatment effect.

An embodiment of the present disclosure further provides an apparatus for driving a multi-leaf collimator. The apparatus includes:

a processor; and a memory for storing an instruction executable by the processor, wherein the processor is configured to:

determine, according to a treatment plan, a target radiation field to be formed;

inquire, from a preset corresponding relationship between radiation fields and driving modes, a target driving mode corresponding to the target radiation field; and control leaves to move according to the target driving mode.

An embodiment of the present disclosure further provides a storage medium having an instruction stored therein. When running on a terminal, the storage medium causes the terminal to execute the method for driving the multi-leaf collimator shown in FIG. 6-2.

An embodiment of the present disclosure further provides a terminal program product containing an instruction. When running on a terminal, the terminal program product causes the terminal to execute the method for driving the multi-leaf collimator shown in FIG. 6-2.

In some embodiments of the present disclosure, a multi-leaf collimator is provided. The multi-leaf collimator includes n leaf-group layers, driving components and a controller, where n is an integer greater than or equal to 2, wherein each leaf-group layer includes one group of leaves or two opposing groups of leaves, each group of leaves includes a plurality of leaves, each of the leaves includes a front end surface and a rear end surface which are opposite to each other, and each of the leaves is movable so that the front end surfaces of the leaves in the multiple leaf-group layers form a variable-shaped region that allows beams to pass through; and the rear end surfaces of the leaves are connected to the driving components, and the controller is configured to control the driving components to drive the leaves to move.

Optionally, at least one of the n leaf-group layers includes two opposing groups of leaves.

Optionally, the leaves in a same leaf-group layer have a same movement direction and the leaves in different leaf-group layers have different movement directions.

Optionally, in the n leaf-group layers, the leaves in any two of the leaf-group layers have a same movement direction and orthographic projections of the leaves in different leaf-group layers in a beam direction partially overlap or do not overlap.

Optionally, in the n leaf-group layers, the leaves in a same leaf-group layer have a same height and leaves in different leaf-group layers have different heights.

Optionally, the leaves in each of the leaf-group layers have a thickness of less than 5 mm.

Optionally, the leaves in each of the leaf-group layers have a height between one-tenth and four times of a half-value layer of a ray.

Optionally, in the n leaf-group layers, any two adjacent leaf-group layers are detachably connected.

Optionally, the multi-leaf collimator further includes guide rails and a guide rail frame, wherein the leaves are located on the guide rails and are movable along the guide rails;

each leaf-group layer is located in one guide rail frame, and in the n leaf-group layers, the guide rail frames of any two adjacent leaf-group layers are detachably connected; or the n leaf-group layers are located in one guide rail frame, and the guide rails of each leaf-group layer are detachably connected with the guide rail frame.

Optionally, the driving component includes a transmission rod and a motor.

The rear end surface of each leaf is connected to the motor through the transmission rod, and the controller is configured to control the motor to drive the transmission rod so as to drive the leaf to move.

In some embodiments of the present disclosure, a radiation therapy head is provided. The radiation therapy head includes a ray source and a radiation field collimation system.

The ray source is configured to emit beams, and the radiation field collimation system includes any multi-leaf collimator according to the first aspect.

In some embodiments of the present disclosure, a method for driving a multi-leaf collimator is provided. The method is applied to the multi-leaf collimator according to the first aspect. The method includes:

determining, according to a treatment plan, a target radiation field to be formed;

inquiring, from a preset corresponding relationship between radiation fields and driving modes, a target driving mode corresponding to the target radiation field; and controlling, according to the target driving mode, the leaves to move.

Optionally, the target driving mode is configured to instruct leaves in different layers to move at different speeds.

The controlling, according to the target driving mode, the leaves to move includes:

controlling, according to the target driving mode, the leaves in different leaf-group layers to move at different speeds.

Optionally, the target driving mode is configured to instruct the leaves in a same leaf-group layer to perform reciprocating movement in a same direction and the leaves in different leaf-group layers to perform reciprocating movement in different directions.

The controlling, according to the target driving mode, the leaves to move includes:

controlling, according to the target driving mode, the leaves in the same leaf-group layer to perform reciprocating movement in the same direction and the leaves in different leaf-group layers to perform reciprocating movement in different directions.

Optionally, each leaf-group layer corresponds to one sub-controller.

The controlling, according to the target driving mode, the leaves to move includes:

according to the target driving mode, controlling, by the sub-controller, the leaves in the corresponding leaf-group layer to move.

Optionally, the controlling, according to the target driving mode, the leaves to move includes:

controlling, according to the target driving mode, the driving components to drive the leaves to move along the guide rails.

In some embodiments of the present disclosure, an apparatus for driving a multi-leaf collimator is provided. The apparatus includes:

a processor; and a memory for storing an instruction executable by the processor, wherein the processor is configured to:

determine, according to a treatment plan, a target radiation field to be formed;

inquire, from a preset corresponding relationship between radiation fields and driving modes, a target driving mode corresponding to the target radiation field; and control, according to the target driving mode, leaves to move.

In some embodiments of the present disclosure, a storage medium having an instruction stored therein is provided. When running on a terminal, the storage medium causes the terminal to execute the method for driving the multi-leaf collimator according to the above third aspect.

In some embodiments of the present disclosure, a terminal program product containing an instruction is provided. When running on a terminal, the terminal program product causes the terminal to execute the method for driving the multi-leaf collimator according to the above third aspect.

In the multi-leaf collimator and the radiation therapy head according to the embodiments of the present disclosure, the multi-leaf collimator includes n leaf-group layers, where n is an integer greater than or equal to 2; and each leaf-group layer includes one or two groups of leaves (for example, the multi-leaf collimator may include two leaf-group layers, wherein the first leaf-group layer includes one group of leaves, and the second leaf-group layer includes two groups of leaves), and each group of leaves includes a plurality of leaves. As the leaves are arranged in multiple layers, the leaves in each layer could have a relatively smaller height and mass. Hence, it is easier to drive the leaves and the movement speed of the leaves can be relatively higher, and thus the difficulty in manufacturing the driving components can be reduced. Moreover, as the driving components have a relatively smaller size and thickness, more leaves can be disposed, thus, the leaves can form a more precise radiation field with more shapes. Therefore, the radiation field can be formed more flexibly. In addition, due to the multiple layers of leaves, the adjustments on the ray intensity and ray dose can also be achieved.

The foregoing descriptions are merely preferred embodiments of the present disclosure, and are not intended to limit the present disclosure. Within the spirit and principles of the disclosure, any modifications, equivalent substitutions, improvements, etc., are within the protection scope of the present disclosure.

The invention claimed is:

1. A multi-leaf collimator, comprising a driving component, a controller and n leaf-group layers, where n is an integer greater than or equal to 2, wherein
   each leaf-group layer comprises one group of leaves or two opposing groups of leaves, each group of leaves comprises a plurality of leaves, each of the leaves comprises a front end surface and a rear end surface which are opposite to each other, and each of the leaves is movable so that the front end surfaces of the leaves in the multiple leaf-group layers form a variable-shaped region that allows beams to pass through;
   the rear end surface of the leaf is connected to the driving component, and the controller is configured to control the driving component to drive the leaf to move; and
   among the n leaf-group layers, at least one leaf-group layer comprises two opposing groups of leaves, and at least one leaf-group layer comprises only one group of leaves.

2. The multi-leaf collimator according to claim 1, wherein the leaves in a same leaf-group layer have a same movement direction and the leaves in different leaf-group layers have different movement directions.

3. The multi-leaf collimator according to claim 1, wherein in the n leaf-group layers, the leaves in any two of the leaf-group layers have a same movement direction and orthographic projections of the leaves in different leaf-group layers in a beam direction do not overlap.

4. The multi-leaf collimator according to claim 1, wherein in the n leaf-group layers, the leaves in a same leaf-group layer have a same height and leaves in different leaf-group layers have different heights.

5. The multi-leaf collimator according to claim 1, wherein the leaves in each of the leaf-group layers have a thickness of less than 5 mm.

6. The multi-leaf collimator according to claim 1, wherein the leaves in each of the leaf-group layers have a height between one-tenth and four times of a half-value layer of a ray.

7. The multi-leaf collimator according to claim 1, wherein in the n leaf-group layers, any two adjacent leaf-group layers are detachably connected.

8. The multi-leaf collimator according to claim 4, further comprising guide rails and guide rail frames, wherein the leaves are located on the guide rails and are movable along the guide rails;

each leaf-group layer is located in one guide rail frame, and in the n leaf-group layers, the guide rail frames of any two adjacent leaf-group layers are detachably connected; or the n leaf-group layers are located in one guide rail frame, and the guide rails of each leaf-group layer are detachably connected with the guide rail frame.

9. A method for driving a multi-leaf collimator, comprising:

determining, according to a treatment plan, a target radiation field to be formed;

inquiring, from a preset corresponding relationship between radiation fields and driving modes, a target driving mode corresponding to the target radiation field; and controlling, according to the target driving mode, leaves to move, wherein the multi-leaf collimator comprises a driving component, a controller and n leaf-group layers, where n is an integer greater than or equal to 2, wherein each leaf-group layer comprises one group of leaves or two opposing groups of leaves, each group of leaves comprises a plurality of leaves, each of the leaves comprises a front end surface and a rear end surface which are opposite to each other, and each of the leaves is movable so that the front end surfaces of the leaves in the multiple leaf-group layers form a variable-shaped region that allows beams to pass through; the rear end surface of the leaf is connected to the driving component, and the controller is configured to control the driving component to drive the leaf to move; and among the n leaf-group layers, at least one leaf-group layer comprises two opposing groups of leaves, and at least one leaf-group layer comprises only one group of leaves.

10. The method according to claim 9, wherein the target driving mode is configured to instruct leaves in different layers to move at different speeds.

11. The method according to claim 9, wherein the driving modes include a driving mode of adjusting a dose via movement speed of the leaves, and a driving mode of adjusting the dose via displacement of the leaves.

12. The method according to claim 9, wherein the target driving mode is configured to control a driving component to drive leaves to move along guide rails.

13. The method according to claim 9, wherein the target driving mode is configured to instruct leaves in a same leaf-group layer to perform reciprocating movement in a same direction and leaves in different leaf-group layers to perform reciprocating movement in different directions.

14. The method according to claim 9, wherein leaf-group layers are controlled by a controller directly, or by a controller through sub-controllers.

15. An apparatus for driving a multi-leaf collimator, comprising:

a processor; and a memory configured to store an instruction executable by the processor, wherein when the instruction is executed by the processor, the instruction causes the processor to:

determine, according to a treatment plan, a target radiation field to be formed;

inquire, from a preset corresponding relationship between radiation fields and driving modes, a target driving mode corresponding to the target radiation field; and control, according to the target driving mode, leaves to move, wherein the multi-leaf collimator comprises a driving component, a controller and n leaf-group layers, where n is an integer greater than or equal to 2, wherein each leaf-group layer comprises one group of leaves or two opposing groups of leaves, each group of leaves comprises a plurality of leaves, each of the leaves comprises a front end surface and a rear end surface which are opposite to each other, and each of the leaves is movable so that the front end surfaces of the leaves in the multiple leaf-group layers form a variable-shaped region that allows beams to pass through; the rear end surface of the leaf is connected to the driving component, and the controller is configured to control the driving component to drive the leaf to move; and among the n leaf-group layers, at least one leaf-group layer comprises two opposing groups of leaves, and at least one leaf-group layer comprises only one group of leaves.

16. The apparatus according to claim 15, wherein the target driving mode is configured to instruct leaves in different layers to move at different speeds.

17. The apparatus according to claim 15, wherein the driving modes include a driving mode of adjusting a dose via movement speed of the leaves, and a driving mode of adjusting the dose via displacement of the leaves.

18. The apparatus according to claim 15, wherein the target driving mode is configured to control a driving component to drive leaves to move along guide rails.

19. The multi-leaf collimator according to claim 1, wherein in the n leaf-group layers, the leaves in any two of the leaf-group layers have a same movement direction and orthographic projections of the leaves in different leaf-group layers in a beam direction partially overlap.

20. The apparatus according to claim 15, wherein in the n leaf-group layers, the leaves in any two of the leaf-group layers have a same movement direction and orthographic projections of the leaves in different leaf-group layers in a beam direction do not overlap.

* * * * *